United States Patent [19]

De Lassauniere et al.

[11] Patent Number: 4,927,755
[45] Date of Patent: May 22, 1990

[54] PROCESS FOR PREPARING POLYNUCLEOTIDES

[75] Inventors: Chabrier De Lassauniere, Paris; Acaye S. Colote, Les Ulis, both of France

[73] Assignee: Societe de Conseils de Recherches et d'Applicatios Scientifiques (S.C.R.A.S.), France

[21] Appl. No.: 265,561

[22] Filed: Nov. 1, 1988

[30] Foreign Application Priority Data

Nov. 2, 1987 [GB] United Kingdom ............... 8725606

[51] Int. Cl.$^5$ .................. C12P 19/34; C07K 3/12; C07K 3/18; C07K 3/20
[52] U.S. Cl. ................... 435/91; 435/814; 435/815; 435/259; 530/412; 530/415; 530/416; 530/417
[58] Field of Search ............... 435/91, 259, 814, 815; 530/412, 415, 416, 417

[56] References Cited

U.S. PATENT DOCUMENTS

| | | | |
|---|---|---|---|
| 3,779,867 | 12/1973 | Katoh et al. | 435/91 |
| 3,850,749 | 11/1974 | Kaufmann et al. | 435/91 |
| 3,917,527 | 11/1975 | Shaltiel | 530/415 |
| 3,935,185 | 1/1976 | Hutchinson et al. | 435/91 |
| 4,000,098 | 12/1976 | Hofstee | 530/415 |
| 4,006,059 | 2/1977 | Butler | 530/415 |
| 4,075,195 | 2/1978 | Roland | 530/415 |
| 4,379,843 | 4/1983 | Cashion et al. | 935/18 |
| 4,617,376 | 10/1986 | Maskalick et al. | 530/415 |
| 4,771,128 | 9/1988 | Ferris et al. | 530/412 |

FOREIGN PATENT DOCUMENTS

| | | | |
|---|---|---|---|
| 2365894 | 9/1976 | Fed. Rep. of Germany | 435/91 |
| 2252350 | 6/1975 | France | 435/91 |
| 0107187 | 8/1975 | Japan | 435/91 |
| 0018597 | 2/1981 | Japan | 435/91 |
| 0619508 | 8/1978 | U.S.S.R. | 435/91 |

OTHER PUBLICATIONS

Cashion et al., Nuc. Acids Res. 8:1167–1185 (1980).

*Primary Examiner*—Herbert J. Lilling
*Assistant Examiner*—Stephanie W. Zitomer
*Attorney, Agent, or Firm*—Lucas & Just

[57] ABSTRACT

This invention relates to a process of preparation of nucleotide polymers wherein a lysate of a bacterial culture is passed successively through three columns (ion exchange resin, hydrophobic resin and molecular sieve), whereby there is obtained a substantially pure polynucleotidephosphorylase solution.

Polymerization of this agent leads to non toxic and non pyrogen products.

This invention relates also to products thus obtained and to therapeutic compositions containing the same.

2 Claims, No Drawings

PROCESS FOR PREPARING POLYNUCLEOTIDES

The present invention relates to an improved process for the obtention of polynucleotides (homo- and copoly-nucleotides) and complexes of the same; the invention relates also to the new improved products thus obtained. Various polynucleotides have been prepared by existing techniques but, so far, most of the obtained products are generally pyrogenic or more or less toxic due to the presence of some impurities or agents appearing in the succession of steps conducting to the desired products. These compounds are adjuvants in various therapeutical fields and more particularly in the treatment of cancer, in the treatment of certain bacterial and viral diseases and for vaccines. The invention relates finally to therapeutic compositions containing these improved polynucleotides as an active ingredient.

Generally, polynucleotides are obtained by the action of a polynucleotide phosphorylase on the appropriate nucleotide monomer. The various possible monomers, such as ADP, CDP, GDP, IDP and UDP, are obtained by well-known techniques. Polynucleotide phosphorylase is also obtained by well-known techniques, starting from a culture of bacteria, then proceeding with a lysis of the bacteria obtained in said culture, followed by extraction of polynucleotide phosphorylase obtained in the lysis from a complex medium, wherein may be found various enzymes, such as kinases, phosphatases, nucleases, diesterases, etc, all products which are competing agents in the further step of polymerisation of the selected nucleotide monomer by the polynucleotide phosphorylase. The presence of the various non-desired enzymes leads to parallel undesired reactions and partial degradation of the monomer to be polymerised as well as the polymer produced.

For these reasons, most of the polynucleotides thus obtained are defective in respect of either or both of their toxicity and their pyrogenic characteristics. Although it may be possible to prepare an acceptably pure polynucleotide phosphorylase on a small scale for analysis purposes or for a limited scientific experimentation, the same is not easily achieved using industrial processing techniques at an acceptable cost.

According to this invention, it has been found possible to obtain in industrially acceptable conditions substantially pure homopolymers, or copolymers, or complexes of polynucleotides or of close analogs of the same, by using, as polymerising agent, instead of the polynucleotide phosphorylase preparations as obtained according to the various methods previously disclosed, a highly purified enzyme free of contaminants leading to undesirable reactions. Close analogs of nucleotides can include 6-hydroxy alkyl derivatives of ADP or 5-halo or 5-OH or 5-methyl derivatives of UDP, for instance.

More particularly, it has been found that, after the culture of a bacteria strain and the lysis of the culture thus obtained, the resulting medium should be passed successively on three columns, the first containing an ion exchange resin such as DEAE Sephacel ® or an equivalent, the second column containing a hydrophobic resin such as phenyl Sepharose ® or an equivalent and the third column containing a molecular sieve such as Sephacryl ® S300 or Sephadex ® 200 or any equivalent.

The product emerging from said third column comprises, essentially but not exclusively, polynucleotide-phosphorylase together with traces of substances devoid of action on the further polymerisation process.

If a homopolymer is desired, the polynucletide-phosphorylase obtained is used for polymerisation of the selected monomer in the presence of usual agents.

If a copolymer is desired, the selected monomer is replaced by a mixture, in appropriate proportions, of the selected monomers. Said copolymer will be designated as Poly A/Poly U.

If a complex is desired, the same polymerisation is undertaken on each of the appropriate monomer and the resultant homopolymers, in the appropriate ratio, are mixed in the presence of NaCl and precipitated with ethanol.

According to an important feature of the invention, the polymerisation of the selected monomer or of the selected mixture of monomers is conducted in conditions which differ from what is usually done. More particularly, concentrations used are far over the usual figures (from about 30 to about 100 times and preferably 50 times or in mmoles/ml from about 0.06 to about 0.2 and preferably about 0.1), the polymerisation is conducted under controlled addition of $MgCl_2$, under controlled pH values from 7.4 to 8.6 and for durations from about 3 to about 6 days.

The resulting polymers or copolymers have a molecular weight range which yields complexes with molecular weights of from about 250 000 to about 1 500 000 with an homogenous polymerisation rate and a polymerisation yield up to 90-95%.

The invention will be better understood from the description of the following succession of five steps, leading from a starting bacteria culture (here E. Coli but other bacteria are also suitable) to a complex of Poly A/Poly U.

Step 1 : Growth of E. Coli B 1/5

The culture is kept in stabs at ambient temperature.

The culture medium contains, per liter, 10 g of NaCl, 10 g of Trypticase and 5 g of yeast extract. After sterilisation for 45 min at 110° C., a separately sterilised glucose solution at 2 g/liter is added. Precultures are made with 10 ml, then 200 ml medium are prepared for a 10 l culture.

Stirring at 470 rpm with 8 l air per min. The doubling time at &600 is 30 mins and the bacteria are harvested at an optical density of 6 at 600 nm. About 8 g per liter of culture are obtained. The pH of the fermentation is controlled at 6.5 to 6.8 by addition of 2N $NH_4OH$. If not immediately used, the culture is to be stored at $-20°$ C.

Step 2 : Lysis of bacteria

---

Buffer A    $5 \times 10^{-2}$ M Tris HCl pH 7.9 (at 25° C.) containing $2 \times 10^{-3}$ M EDTA, 0.233 M NaCl (13.63 g/l) and 5% glycerol (50 ml/l)

Buffer B    $10^{-2}$ M Tris-HCl pH 7.9 containing $10^{-4}$ M EDTA, 0.2 M NaCl and 5% glycerol.

For 165 g bacteria (20 l culture)

---

Just before use, 0.4 ml dithiothreitol (DTT) 0.1 M (15.4 mg/ml) are added to 400 ml buffer A at room temperature, followed by 28 $\mu$l mercaptoethanol, 45 mg lysozyme and 14 mg phenylmethyl sulphonyl fluoride (PMSF) dissolved in 4 ml ethanol. The frozen bacteria (165 g) are dispersed in this medium in a mixer (final temperature $\sim 10°$ C.), and the suspension allowed to warm to 15° C. with occasional mixing (about 20 minutes), then 272 mg sodium deoxycholate are added with mixing, followed by 4 mg deoxyribonuclease (DNAase). The lysis mixture is left for 20 minutes with occasional mixing and the temperature kept at 20° C. To this is added 400 ml buffer B plus 0.4 ml 0.1 M DTT with mixing, and the suspension centrifuged at 16 000 g (10 000 rpm in Sorvall centrifuge) for 1 hour at 5° C.

DNAase 50 679 Dornase units/mg.
Lysozyme 25 000 units/mg.

The supernatant (~900 ml) from centrifugation was diluted to 1 liter with distilled water and protein precipitated by addition of 280 g ammonium sulphate (45% saturation) at 4° C. with stirring and the mixture left at 4° C. for 2 hours. Protein was recovered by centrifugation at 16 000 g for 30 minutes at 5° C. The precipitate (supernatants are discarded) was dissolved in 150 ml $10^{-2}$ M Tris HCl pH 7.8 and the solution centrifuged for 20 minutes at 16 000 g to remove insoluble material. The supernatants were dialysed against 4 changes of 2 l of $5 \times 10^{-2}$ M Tris HCl pH 7.8 at 4° C. over 18 hours then the solution was centrifuged for 1 hour at 16 000 g to remove insoluble material.

300 ml, pH 7.8, conductivity <7.0 mS.

Step 3 : Purification of Polynucleotide *Phosphorylase coli* B 1/5 (PNPase)

1. The above supernatants were run on to a column of 280 ml DEAE Sephacel (40×3 cm) equilibrated in 0.1 M Tris HCl pH 7.4 at 4° C. and the column eluted with a gradient of 1 liter 0.1 M Tris HCl pH 7.4 to 1 liter 0.1 M Tris HCl in 0.4 M NaCl pH 7.4 collecting 10 ml fractions. A peak of diesterase activity is eluted followed by a second peak of polynucleotide phosphorylase activity localised in fractions 105 to 125 eluted at 0.21 M NaCl 0.1 M Tris HCl.

Volume 210 ml : 107 units/ml Total 22 470.

2. This solution was adjusted to 0.5 M in ammonium sulphate by addition of 28 g with stirring then run on to a column of 60 ml phenyl sepharose (19×2 cm) equilibrated in 0.5 M $(NH_4)_2SO_4$ 0.05 M Tris HCl pH 7.4. The column was washed with about 20 ml 0.5 M $(NH_4)_2SO_4$ in 0.1 M Tris HCl pH 7.4 then eluted with a reverse gradient of 250 ml 0.4 M Tris HCl pH 7.8 in 0.1 M $(NH_4)_2SO_4$ to $3 \times 10^{-3}$ M Tris HCl pH 7.8 at 4° C. Approximately 10 ml fractions. Active fractions were grouped.

Volume 55 ml : 355 units/ml Total 19 525.

3. Ammonium sulphate (20 g) was added with stirring (55% saturation) to precipitate protein and the precipitate left at 4° C. for 1 hour then centrifuged 15 minutes at 16 000 g. The residue was dissolved in a minimum of 0.1 M NaCl 0.05 M Tris HCl pH 7.4 (about 10 ml) and the solution applied to a column of 350 ml Sephacryl S300 (50×3 cm) equilibrated in 0.1 NaCl 0.05 M Tris HCl pH 7.4 and the enzyme eluted with the same buffer (approximately 10 ml fractions). Active fractions (13–17) were grouped.

Volume 60 ml : 312.5 units/ml Total 18 750.
540 units. $\delta 280$

The enzyme was precipitated by addition of 26 g $(NH_{42}SO_4$ (65% saturation) and the suspension stored at $-30°$ C.

Step 4 : Preparation of Polymers 100 g of ADP $Na_2$ (or 100 g UDP $Na_3$) are dissolved in about 600 ml of water and added to :

200 ml M. Tris HCl pH 8.3
250 ml M. ammonium acetate
20 ml 0.1 M EDTA pH 8.0
100 ml M. $MgCl_2$ in a 2 l bottle. The volume was completed to 2 l with water and the pH adjusted to 8.6 at room temperature with 5 $N.NH_4OH$. The surface was covered with a layer of toluene. Nucleoside diphosphates used should be free of contaminating metals such as $Fe^{3+}$ or $Cu^{2+}$.

To an aliquot of the above mixture (80 ml) was added 200 units of enzyme and 2 ml of a previous preparation of poly A (or poly U) as primer and the solution was incubated at 37° C. for 2 hours then transferred to the main batch which was kept at 37° C. After 4 hours a further 300 units of enzyme was added and the incubation continued. The pH drops to about 8.3 after 24 hours and the pH is thereafter maintained at 8.0 to 8.3 by addition of 5 $N.NH_4OH$.

Total units of enzyme=500 i.e. 5 units per g. If polymerisation proceeds at less than 25% per 24 hours more enzyme can be added to increase the rate at suitable times.

Additional quantities of 25 ml M. $MgCl_2$ are added with vigorous stirring at about 30%, 55% and 75% polymerisation (total 175 mmoles Mg for 200 nmoles ADP or UDP), the pH being maintained at 8.0 to 8.3 (measured at 37° C). Polymerisation should be 80–90% at the end of three to four days.

Stepwise addition of the $MgCl_2$ maintains the ratio of free ADP (UDP) to Mg at about 2 at the polymerisation levels mentioned above.

At the end of the incubation, the mixture is centrifuged to remove the precipitated ammonium magnesium phosphate, the precipitate being washed with a little water and the combined supernatants used to prepare the complex poly A - poly U.

Optimal conditions of polymerisation are pH 8.0 to 8.3 with stepwise addition of $MgCl_2$ and sufficient enzyme to have a rate of polymerisation of about 30% per day. Higher incubation pH (8.3 to 8.6) gives smaller polymers. Addition of total Mg at the beginning of incubation also gives smaller polymers.

Step 5 : Preparation of complex Poly A - Poly U

Total nucleotide content of the solutions is determined by hydrolysis of the incubation mixture in 0.1 N NaOH at 100° C. for 5 minutes using a dilution of 1000 for poly A and 500 for poly U (e.g. 10 μl poly A or 20 μl poly U in 10 ml 0.1. N NaOH or more precisely by intermediate dilution of 100 μl A and 200 μl U). Absorption at 260 nm is measured and molarity estimated using the following values.

| $\delta_{260}$ nm $\times 10^{-3}$ for molar solutions. | | |
|---|---|---|
| | pH 7.0 | 0.1 N NaOH (hydrolysis) |
| Ap | 15.3 | 15.3 |
| Poly A | 9.8 | 15.3 |
| Up | 10.0 | 7.7 |
| Poly U | 9.5 | 7.7 |

Polymer concentrations are determined from total nucleotide and percentage polymerisation. Volumes for a stoichiometric ratio A/U=1:1 are then calculated. To the poly U in a 10 l bottle is added 200 ml 25% aqueous NaCl fOllowed by the solution of poly A and the solutions thoroughly mixed (final concentration of NaCl~0.18 M) then left at 4° C. for a minimum of 3 hours.

An equal volume of ethanol is then added with stirring to precipitate poly A - poly U and the mixture left at 4° C. for one hour. The complex is collected by centrifugation in a Sorvall 3 B (1 liter pots) at 5000 rpm for 3 minutes, then washed with 2 l of 55% ethanol. The residue is dissolved in about 4 l pure water and centrifuged to remove any traces of ammonium magnesium phosphate. To the clear supernatants are added 200 ml 25% NaCl and the solution left at 4° C. for a minimum of three hours.

The complex is again precipitated by addition of an equal volume of ethanol with stirring, collected by centrifugation, washed with 55% ethanol (about 2 l), 75% ethanol and twice with 96% ethanol, then dried under vacuum.

Yield about 110-120 g.

As rule, for precipitation of the complex with 50% ethanol, NaCl (0-M to 0.02 M) must be present. For washing, not less than 55% aqueous ethanol must be used (the precipitated complex is dissolved by 50% ethanol).

TOXICITY $LD_{50}$ has been researched on mice and rats by IP and IV routes.

No death was noticed at the maximum administration doses IV, either on mice or on rats.

No death was also noticed on IP administration on rats but a $LD_{50}$ of about 3 g/kg was found on mice IP.

Usual pyrogen tests were fully negative.

PHARMACOLOGY

As the polymers and copolymers according to the invention are generally known but which, up to now, were never obtained industrially in a sufficiently pure state, various pharmacological experimentations have been conducted for years on samples of specially purified products which were not really obtainable at reasonable commercial conditions.

All the interest of the invention may be appreciated from the existing bibliography and for instance the following article:

- MODULATION OF THE IMMUNE SYSTEM BY SYNTHETIC POLYNUCLEOTIDES—A.G. JOHNSON—Springer Semin. Immunopathol., 2, pp 149-168 (1979),
- REGULATION OF THE IMMUNE SYSTEM BY SYNTHETIC POLYNUCLEOTIDES —I. Characteristics of Adjuvant Action on Antibody Synthesis—J.R. SCHIDTKE and A.G. JOHNSON—J. Immunol., 106, pp 1191-1200 (1971),
- CHANGES IN LYMPHOCYTE SUBPOPULATIONS IN MICE RECEIVING A SINGLE INJECTION OF POLY A—POLY U—M. DONNER, D. VALLIER and F. LACOUR—Ann. Immunol. (Inst. Pasteur) 128C, pp 1039-1052 (1977),
- SPECTRUM AND MODE OF ACTION OF POLY A—POLY U IN THE STIMULATION OF IMMUNE RESPONSES—V. BRAUN, M. ISHIZUKA, U. YAJIMA, D. WEBB and R. WINCHURCH in : BEERS R.F., BRAUN W., "Biological effects of polynucleotides" New-York : Springle-Verlag, pp 139-156 (1971),
- REDUCED INCIDENCE OF SPONTANEOUS MAMMARY TUMORS IN C3H/He MICE AFTER TREATMENT WITH POLYADENYLATE-POLYRIDYLATE—F. LACOUR, G. DELAGE and C. CHIANALE—Science, 187, pp 256-257 (1975),
- POLY A—POLY U AS AN ADJUNCT TO SURGERY IN THE TREATMENT OF SPONTANEOUS MURINE MAMMARY ADENOCARCINOMA—F. LACOUR, J. LACOUR and A. SPIRA—Recent Results in Cancer Research, vol. 47, pp 352-356,
- POLYADENYLIC-POLYURIDYLIC ACID BIOLOGICAL RESPONSE-MODIFYING ACTIVITIES IN MICE. IN VIVO ORGAN DISTRIBUTION AND PHARMACOKINETICS IN RABBITS —F. LACOUR—J. Biol. Resp. Modif., 4, pp 490-494 (1985)
- A PHASE I CLINICAL TOLERANCE STUDY OF POLYADENYLIC-POLYURIDYLIC ACID IN CANCER PATIENTS—J.P. DUCRET, P. CAILLE, H. SANCHO-GARNIER, J.L. AMIEL, M. MICHELSON, R.G. HOVANESSIAN, J.K. YOUN and F. LACOUR—J. Biol. Resp. Modif., 4, pp 129-133 (1985).

PRESENTATION and POSOLOGY

Prefered mode of administration is by IV of an isotonic solution containing 0.01 to 0.1 g of active ingredient. A weekly injection will be repeated for 6 weeks.

We claim:

1. A process for preparing polymers of nucleotides comprising the following sequence of steps:

inducing the lysis of a bacteria strain culture and passing the resulting medium successively through three columns:

the first one containing an ion exchange resin, the second one containing a hydrophobic resin and the third one containing a molecular sieve, which treatment leads to a polynucleotidephosphorylase solution substantially pure with regard to substances that might affect a further polymerisation process, treating a selected nucleotide by the phosphorylase thus obtained, comprising reacting from about 200 to about 750 phosphorylase units in a solution containing the usual buffers and a concentration of 0.06 to 0.2 mmoles/ml of the selected mononucleotide in the presence of $MgCL_2$, stepwise added for controlling the polymerisation level, for a duration of about 3 to about 6 while keeping the pH values between 7.4 and 8.6, separating and washing the polymer thus obtained, whereby a substantially non-pyrogenic and/or substantially non-toxic polymer is obtained.

2. The process of claim 1 wherein, between the steps of treating and separating, the process further comprises the steps of treating a second selected nucleotide by the phosphorylase thus obtained, comprising reacting from about 200 to about 750 phosphorylase units in a solution containing the usual buffers and a concentration of 0.06 to 0.2 mmoles/ml of the selected second mononucleotide in the presence of $MgCl_2$, stepwise added for controlling the polymerisation level, for a duration of about 3 to about 6 days while keeping the pH values between 7.4 and 8.6, mixing appropriate amounts of each selected polymer thus obtained in water in the presence of NaCl and finally precipitating the resulting complex by addition of ethanol.

* * * * *

UNITED STATES PATENT AND TRADEMARK OFFICE
CERTIFICATE OF CORRECTION

PATENT NO. : 4,927,755

DATED : May 22, 1990

INVENTOR(S) : Pierre Chabrier De Lassauniere et al.

It is certified that error appears in the above-identified patent and that said Letters Patent is hereby corrected as shown below:

On the face of the patent, reference [75], 1st Inventor's name should read --Pierre-Etienne C. De Lassauniere--

Column 2, line 45, change "&" to --$\delta$--

Column 3, line 58, change "(NH42SO4" to --$(NH_4)_2SO_4$--

Column 4, line 59, change "fOllowed" to --followed--

Column 5, line 12, change "O-M" to --0.15M--

Column 6, line 7, after "ACID" insert --:--; line 45, after "6" insert --days--.

Signed and Sealed this

Ninth Day of July, 1991

Attest:

HARRY F. MANBECK, JR.

Attesting Officer

Commissioner of Patents and Trademarks